United States Patent [19]

Schwartze et al.

[11] Patent Number: Plant 5,674

[45] Date of Patent: Feb. 25, 1986

[54] STRAWBERRY PLANT-BURLINGTON

[75] Inventors: Chester S. Schwartze, Puyallup, Wash.; Atsusa Sakuma, deceased, late of La Conner, Wash., by Grace Insakuma, executrix

[73] Assignee: Sakuma Bros. Farms, Inc., Burlington, Wash.

[21] Appl. No.: 594,799

[22] Filed: Mar. 30, 1984

[51] Int. Cl.[4] ..... A01H 5/03

[52] U.S. Cl. ..... Plt./49

[58] Field of Search ..... Plt./49

*Primary Examiner*—Robert E. Bagwill

*Attorney, Agent, or Firm*—Hughes, Barnard & Cassidy

[57] ABSTRACT

A new, distinct variety of weak-day-neutral strawberry plant is characterized by sustained, large size fruit borne in long, loose clusters from June to October with peak production in August; fruit characteristics that adapt it to both gardening and fresh market; a plant of exceptional size, capable of maintaining uniform size and vigor.

3 Drawing Figures

BACKGROUND OF THE NEW PLANT

This invention relates to a new and distinct variety of everbearing (weakly day-neutral) strawberry plant designated Burlington. It originated as a seedling from a cross made in 1978 between the non-everbearing cultivar Tufts, U.S. Plant Pat. No. 3,561, and an everbearing strawberry known only as E.B. 18, originated by the U.S. Dept. of Agriculture at Beltsville, Md. from the cross MdUS 3082xCal.65.65.-601 (day-neutral), neither of the latter of which has been patented.

Burlington bore its first fruit in 1979 at Sakuma Bros. Farm, Inc., in Burlington, Wash. It was selected and assigned selection number SS 534. It has been tested and evaluated under this number by the originators on farms owned and operated by the present assignee, in comparison with Quinault, which is the principal everbearing cultivar now grown in the Pacific Northwest. Characteristics have been noted that distinguish Burlington from the established everbearers known as Aptos, Brighton, Ft. Laramie, Hecker, Osark Beauty and Quinault and the recently introduced Fern, Selva, Tillicum, Tribute and Tristar; of all of the aforenoted, however, it most nearly resembles Selva. Similarities and differences between Burlington and Selva are noted below.

Plants of Burlington have been propagated asexually by separation of runner plants from the original seedling plant and by subsequent propagation of the runners. Typical runner plants were virus-indexed by standard methods and those that indexed "virus-free" were heat-treated to inactivate possible remaining heat-labile viruses. The most vigorous plant resulting from those procedures was then increased by meristem culture, and was yet further increased by screenhouse culture as required for purposes of certification by the Washington State Dept. of Agriculture.

DESCRIPTION OF THE DRAWINGS

The photographic color reproductions herewith depict the principal identifying characteristics of Burlington as follows.

DESCRIPTION OF THE NEW PLANT

Burlington is readily distinguished from other everbearers by one or more of these characteristics:

(1) It is weakly day-neutral (like Selva), producing relatively few flower clusters in spring, a light fruit crop in June and early July, increasing to heavy production in August.

(2) The plant is one of the largest of all everbearers, often exceeding 12" in height (at Burlington, Wash.) and 18"-22" in total width. Of recent introductions only Selva plants are as large.

(3) The leaflets, usually 3, occasionally 4 or even 5, are large, often about 4" long by about 4.5" in diameter, rounded, upward-cupped, firm and thick. Petioles are stout and often from about 9" to about 10" long as measured from the base. Selva also has long petioles but the leaflet is more elongated, thinner and essentially flat.

Figure 1:
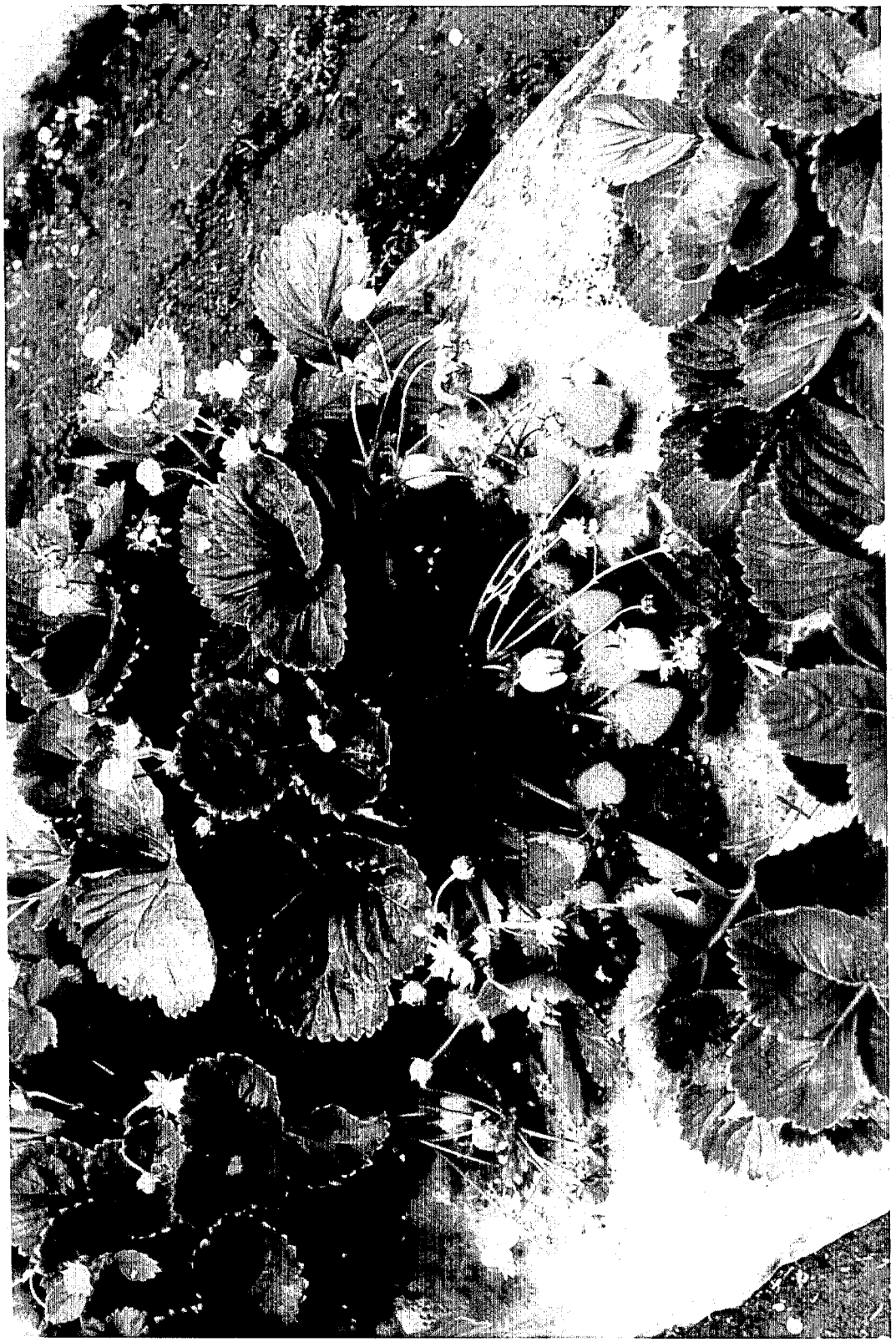
FIG. 1 shows a repesentative first-year plant in August growing on plastic mulch, with typical large, long-stemmed fruits in long, loose clusters.
Figure 2:
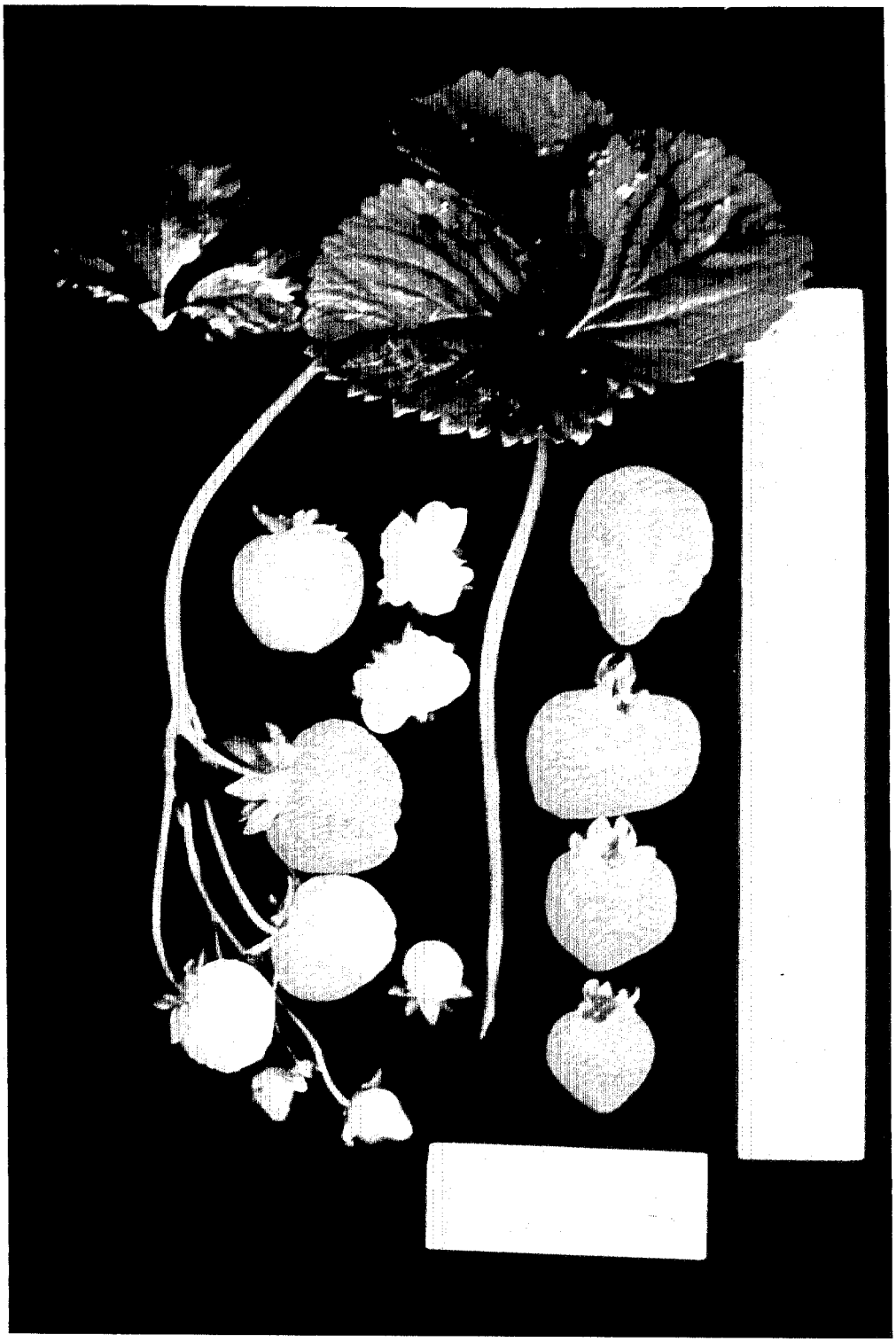
FIG. 2 shows a typical fruit cluster with a long peduncle (partially hidden), along with a typical midsummer leaf. A series of fruits of illustrative sizes and shapes are shown, one in longitudinal section. Customary large primary flowers are included in the figures, showing as well a small leaf exhibiting a white streak, an inherited foliar abnormality that appears temporarily in spring and early summer in some Burlington plants.
Figure 3:
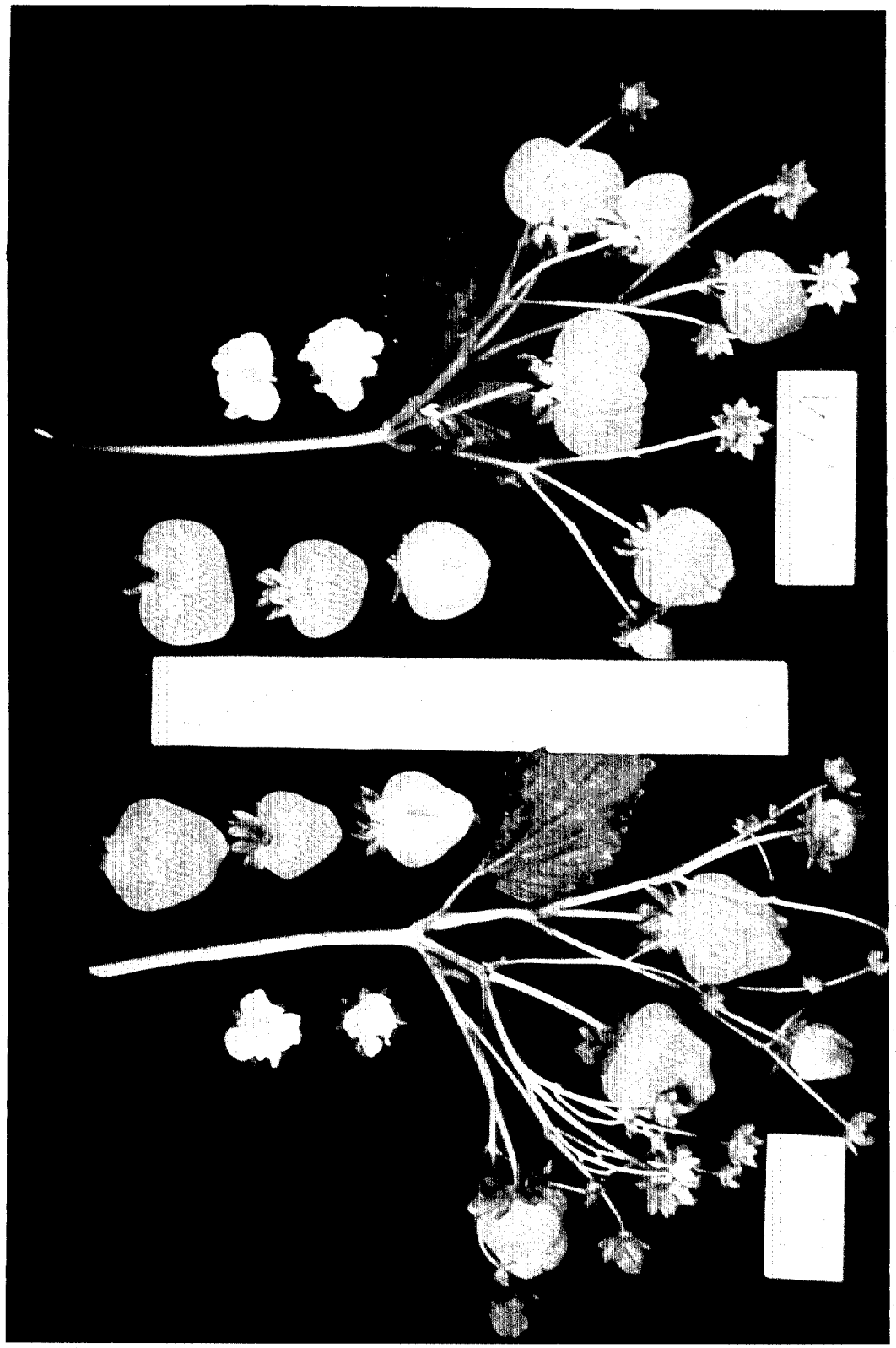
FIG. 3, shows comparative fruit clusters, fruits and flowers of Burlington and Selva.

(4) Flower clusters at Burlington have long peduncles, are visible among the leaves, not above them as best viewed in FIG. 1.

(5) Primary flowers are exceptionally large, up to 2" in diameter, often with 10 to (rarely) 16 petals and petaloides and as many sepals. The milk-white petals are nearly equilateral, ranging to 11-13 mm. with distinctly wavy margins.

(6) Fruit clusters are typically long, simply and loosely constructed, often with only 4-6 fruits on 2"-3" pedicels. The peduncles are commonly 5"-6" long, the clusters overall near 12" long and borne down onto the soil or mulch where the fruits are clearly visible. In general the fruit clusters resemble those of the female parent, Tufts.

(7) Fruit size is more consistently large than with any other everbearer; only Selva has as large primaries. Vigorous plants of Burlington typically produce no small berries.

(8) Fruit shape is basically long-conic but some of the largest fruits are broad, thick and blunt, somewhat furrowed and may be green-tipped or form a black "button". Selva fruits are more uniform in shape with no green tips.

(9) Fruit color is glossy light to medium orange-red, seeds yellow, medium size, flush to slightly raised. If picked at the "pink" stage, coloring proceeds and the green tips largely disappear.

(10) The calyx is medium large, not quite as large nor as bright green as Selva's and a little more reflexed.

(11) The White Streak abnormality, also in the parent E.B.18, has appeared every year in Burlington but not at all in other everbearing cultivars. It consists of white areas or "streaks" in parts of leaf blades, sometimes in margins, rarely in flower clusters. Symptoms have appeared in late spring, peaking in May-June, sometimes slightly depressing plant growth but not noticeably affecting fruit production; new leaves in late summer have been normal.

(12) Other observations:

Exceptional fruit size has characterized Burlington throughout the testing period. Counts of fruits per pound have often been under 20 for early pickings of Burlington and commonly 18–24 when Quinault counts were 28–34.

Fruit stems are tough and adhere well to the fruit; the calyx (cap) adds to the attractiveness of the fruit. The skin is fairly tough. Holding tests have indicated excellent retention of gloss and a relatively long shelf life.

Flesh color is attractive light orange-red with lighter core area. Flesh texture is firmer and more pleasant to the palate than that of Quinault. Pressure tests with a 3 mm. plunger averaged 130 grams for Burlington when Quinault averaged 80 grams.

Flavor is good though less rich than in the best June-croppers, sweeter than in Quinault, not quite as sweet as in Sakuma. A taste panel has consistently rated Burlington superior to Quinault in taste, palatability and attractiveness both as fresh fruit and after freezing and thawing.

The flowers have many large anthers and abundant pollen at all times.

Leaf color, useful in field identification, is nearly the same as in Selva, slightly lighter than in Sakuma, noticeably lighter than in Tribute or Tristar, darker than in Tillicum.

Crown multiplication in Burlington is neither rapid nor excessive.

Runners are long, strong and numerous.

In yield, Burlington has been superior to Quinault chiefly because all the fruit has been large. Yield has been significantly increased by the use of plastic mulch.

Systematic assessment for powdery mildew infection in the field has shown that Burlington is much less susceptible than Quinault. In plots surrounded by virus-infected plants, Burlington has degenerated less rapidly than Quinault and some other selections.

Because its fruits are consistently large and glossy and have good shelf life together with good fruit quality, Burlington should be of interest for fresh fruit marketing as well as for garden uses.

What is claimed is:

1. The new and distinct variety of everbearing strawberry plant herein described and illustrated and identifiable by reference to the characteristics enumerated and described above.

* * * * *